(12) United States Patent
Tunius

(10) Patent No.: US 8,697,932 B2
(45) Date of Patent: Apr. 15, 2014

(54) SWITCHABLE ADHESIVES

(75) Inventor: Mats Tunius, Göteborg (SE)

(73) Assignee: Lumina Adhesives AB, Gothenburg (SE)

( * ) Notice: Subject to any disclaimer, the term of this patent is extended or adjusted under 35 U.S.C. 154(b) by 213 days.

(21) Appl. No.: 13/120,725

(22) PCT Filed: Sep. 24, 2009

(86) PCT No.: PCT/GB2009/002280
§ 371 (c)(1),
(2), (4) Date: Jun. 6, 2011

(87) PCT Pub. No.: WO2010/034998
PCT Pub. Date: Apr. 1, 2010

(65) Prior Publication Data
US 2011/0224593 A1    Sep. 15, 2011

Related U.S. Application Data

(60) Provisional application No. 61/099,625, filed on Sep. 24, 2008.

(30) Foreign Application Priority Data

Mar. 17, 2009  (GB) .................................. 0904582.4

(51) Int. Cl.
*A61F 13/00* (2006.01)
*C08F 2/46* (2006.01)
*C08F 2/48* (2006.01)
*C09J 7/02* (2006.01)

(52) U.S. Cl.
USPC .................. 602/54; 602/41; 602/57; 522/26; 522/66; 522/174; 522/183

(58) Field of Classification Search
USPC ........ 428/343, 345, 346, 354; 602/41–43, 52, 602/57–58; 3/343, 345, 346
See application file for complete search history.

(56) References Cited

U.S. PATENT DOCUMENTS 4,286,047 A    8/1981    Bennett et al.
4,331,576 A    5/1982    Colon et al.

(Continued)

FOREIGN PATENT DOCUMENTS

EP    0863775    10/2000
JP    3043988    5/2000

OTHER PUBLICATIONS

International Search Report for International Patent Application No. PCT/GB2009/002280 issued Apr. 1, 2010.

*Primary Examiner* — Kim M Lewis
(74) *Attorney, Agent, or Firm* — Lowenstein Sandler LLP

(57) ABSTRACT

Switchable adhesives comprising a mixture, in proportions by weight, of 20% to 98% of an adhesive, 2% to 80% of curable molecules and 0.05% to 10% of photoinitiator. Preferably, the adhesive and curable molecules are mutually soluble when dry or the curable molecules and adhesive may be uniformly dispersed in each other. Preferably the amount of adhesive in the mixture is in the range 40% to 98% by weight, more preferably 60% to 95% by weight, even more preferably 70% to 85% by weight. Preferably the proportion of curable molecules in the mixture ranges from 2% to 60% by weight, more preferably 5% to 40% by weight, even more preferably 15% to 30% by weight. Preferably, the photoinitiator is present in the mixture in the proportions 0.5% to 5% by weight, more preferably 1% to 3% by weight. Such switchable adhesives are useful in medical dressings and other removable sheet products, and may be simply prepared by stirring the adhesive, the curable molecules and the photoinitiator together at room temperature.

20 Claims, 3 Drawing Sheets

(56) References Cited

U.S. PATENT DOCUMENTS

| | | | |
|---|---|---|---|
| 4,968,559 A | 11/1990 | Kuroda et al. | |
| 4,999,242 A | 3/1991 | Ishiwata et al. | |
| 5,032,637 A | 7/1991 | Therriault et al. | |
| 5,118,567 A | 6/1992 | Komiyama et al. | |
| 5,182,323 A | 1/1993 | Russell | |
| 5,187,007 A | 2/1993 | Ebe et al. | |
| 5,352,516 A | 10/1994 | Therriault et al. | |
| 5,747,551 A | 5/1998 | Lewandowski | |
| 5,942,578 A | 8/1999 | Noguchi et al. | |
| 5,955,512 A | 9/1999 | Numazawa et al. | |
| 6,184,264 B1 | 2/2001 | Webster | |
| 6,610,762 B1 | 8/2003 | Webster | |
| 6,841,587 B2 | 1/2005 | Yamamoto | |
| 2004/0151902 A1* | 8/2004 | Ansell | 428/343 |

* cited by examiner

SWITCHABLE ADHESIVES

The present invention relates to adhesives, more particularly to pressure sensitive adhesives which are "switchable" from a tacky state to a non-tacky or low-tack state such that the switched adhesive has a reduced peel strength. The present invention also relates to methods for producing switchable adhesives and to articles comprising switchable adhesives.

In particular, the present invention provides benefits in situations where strong adhesion to fragile surfaces is required. Should it then become necessary to release the fragile surface, the adhesive can be switched to its low-tack state and removed from the fragile surface completely without harming it.

Certain adhesive products, such as adhesive surgical or medical dressings and bandages normally comprise a layer of a pressure sensitive adhesive. However, when a conventional adhesive dressing and/or bandage is removed from the patient's skin, it can often cause localised trauma and/or pain to the patient. This is particularly true for patients with a long term condition that requires an adhesive dressing to be applied to the same part of the body repeatedly over a prolonged period, such as stoma patients. It is also true for patients with fragile skin, especially the elderly and children.

Therefore, a need has been identified to provide adhesive dressings, for example, which are able to undergo a reduction in peel strength of the adhesive, and therefore cause less localised trauma to the patient's skin upon removal of the dressing, compared to a dressing using a conventional adhesive. Further, a need has been identified to provide such adhesive dressings where the reduction in peel strength can be achieved in a controlled manner in a relatively short time, say from a number of seconds to a few minutes.

For convenience, the term "switchable" will be used to refer to adhesives which can be changed from a tacky to a non-tacky state or, more accurately, to a low-tack state. Recognizing that the expression "low tack" is a relative term, it will be defined here as meaning the condition of minimum tackiness which the adhesive reaches after switching from its tacky state. The reduction in peel force may be as great as 99% or as little as 30%. Typically, the reduction in peel force is between 70% and 90%.

Examples of known switchable adhesives may be found in U.S. Pat. Nos. 5,032,637, 5,352,516, 4,331,576 and 5,182,323 which describe adhesives that become less tacky, i.e., are switchable, upon contact with water. However, such adhesives are unsuitable if used on a wound dressing and the patient's wound needs to be kept dry.

UV switchable adhesives are described in U.S. Pat. Nos. 4,286,047, 4,968,559, 5,118,567, 5,187,007 and Japanese Patent No. 3043988. The adhesives disclosed in these documents suffer from the disadvantage that they require high doses of UV radiation and need to be used in conjunction with photoinitiators that would be regarded as hazardous if used in medical applications requiring skin contact. Since it is undesirable to expose patients to too much ultra violet radiation, these earlier patents do not satisfy the need for a switchable adhesive which can undergo a reduction in peel strength at low dosages of UV radiation or, more preferably, by exposure to visible light irradiation.

European Patent No. EP 0863775 and U.S. Pat. Nos. 6,184,264 and 6,610,762 disclose adhesives which are switchable when exposed to, inter alia, visible light, i.e., are visible light switchable or are switchable upon exposure to low dosages of UV light. The visible light switchable or low dosage UV light switchable adhesives described in these documents generally comprise an acrylic adhesive based on copolymers of alkyl acrylates, acrylic acid and/or a free radical polymerisable vinyl moiety "modified" or functionalised by a curable moiety bound thereto. Typical of the bound-in curable moieties are those derived from anthracenes, cinnamates, maleimides, coumarins, acrylates and/or methacrylates.

United States published patent application No. US 2004/0019127 A1 discloses a UV-curable pressure-sensitive adhesive composition comprising a photoinitiator with a molar absorptivity at 365 nm of at least 1,000 mol-1.cm-1 and a maximum absorption wavelength of at least 420 nm on a long wavelength side; and an adhesive sheet having a layer of the composition disposed over a photo-transmitting base film. The pressure-sensitive adhesive sheet can be cured by exposure to ultraviolet rays even at a low intensity or for short time, which contributes to energy saving and productivity improvements as a sheet for processing, fixation or surface protection of a semiconductor wafer.

U.S. Pat. No. 4,999,242 discloses an adhesive tape having an adhesive curable by irradiation, for example by ultra violet rays or ionising radiation such as an electron beam, comprising a radiation-curable adhesive layer which is fowled on a radiation transmitting-substrate. The radiation-curable adhesive layer is composed of an acrylic adhesive, a compound having carbon-carbon double bonds and a silicone acrylate compound. The radiation-curable tape can be used in processing steps for the production of semiconductor wafers, ceramics and glass employing a direct picking-up system.

U.S. Pat. No. 5,942,578 discloses an energy beam curable pressure sensitive adhesive composition which comprises at least two energy beam curable copolymers having energy beam polymerizable groups in side chains thereof. The adhesive composition has satisfactory adhesive strength before irradiation with the energy beam and can be cured by irradiation to a degree such that the amount of adhesive residue remaining on an adherend after peeling is extremely small. The composition ensures excellent expansibility at the expanding step and excellent recognition at the time of pickup. Also, the composition exhibits high work efficiency because of very low pickup strength at the bonding step, irrespective of the execution of the expanding step.

U.S. Pat. No. 5,955,512 discloses a pressure sensitive adhesive composition comprising an acrylic copolymer (A), an energy beam polymerizable urethane acrylate oligomer (B) and an energy beam polymerizable compound having one acryloyl group or methacryloyl group in each molecule thereof (C). The composition preferably also contains a plasticizer (D), a crosslinking agent (E) and/or a photo-polymerization initiator (F) according to necessity. The pressure sensitive adhesive composition has satisfactory pressure sensitive adherence and initial adhesion before irradiation with an energy beam and the adhesive strength thereof is sharply reduced whilst maintaining its elasticity after irradiation. The pressure sensitive adhesive composition is said to ensure excellent chip alignability in the expanding step subsequent to dicing.

One problem associated with the use of adhesives which are functionalised by bound-in curable groups is the difficulty in synthesis. The polymerisation of some prior art functionalised adhesives requires the use of multiple solvents in order to:
(a) produce a polymer having a sufficiently high molecular weight and low monomer concentration for it to be used as a medical adhesive, and
(b) carry out the reaction between the functionalising moiety and the main polymer chain.

An adhesive manufacturing process requiring multiple solvents, and hence solvent exchange steps, becomes complicated, time-consuming and expensive. There may also be environmental concerns about disposal of waste solvents.

The present invention has been made in view of the above disadvantages of known switchable pressure sensitive adhesive systems and provides the following advantages:

(1) Adjustment of performances such as switch %, switch time, peel strength, etc. is easier and more quickly done by changing the ingredients in a mixture or by changing the concentration of them, rather than synthesising a new adhesive polymer.
(2) The production time for a switchable adhesive based on a mixture is a few hours, while that for synthesising a switchable adhesive polymer as described in the prior art is a matter of days.
(3) By using a higher number of curable molecules in a switchable adhesive based on a mixture compared to that which can be achieved in a switchable adhesive having bound-in curable groups, the decrease of tackiness can be made greater while the switch time can be brought down to seconds rather than minutes.
(4) The concentration of the most expensive component, the photoinitiator, can be decreased considerably compared to the amount of photo initiator required in a prior art switchable adhesive.
(5) The switchable adhesive according to the invention can be made using commercially available ingredients at a comparable low price and supplied in an ample variation; the end cost of the adhesive is much less compared to "in house" synthesised switchable adhesive polymers.
(6) The production hazard is much less for a switchable adhesive based on a mixture rather than based on a switchable adhesive polymer because it is done under ambient temperature without any chemical reaction taking place which minimizes the risk of gelling in production vessels or runaway exothermic reactions.

An embodiment of the present invention provides an improved switchable adhesive formulation which can be manufactured without the use of multiple solvents. An embodiment of the present invention provides an improved switchable adhesive system which undergoes transformation from a tacky state to a non-tacky state in a relatively short period of time compared to known switchable adhesive systems. An embodiment of the present invention provides an improved switchable adhesive system which undergoes transformation from a tacky state to a non-tacky state upon exposure to visible light and without requiring exposure to UV radiation.

In a first aspect, the invention is a pressure sensitive switchable adhesive composition comprising a mixture, in proportions by weight, of 2% to 80% of curable molecules and 0.05% to 10% of photoinitiator, the balance being adhesive and incidental constituents. Preferably, the adhesive and curable molecules are mutually soluble when dry, although good results are obtained when the curable molecules are uniformly dispersed in the adhesive, said adhesive and curable molecules being mutually insoluble or only partly mutually soluble when dry.

Preferably the amount of adhesive present in the mixture is in the range 40% to 98% by weight, more preferably 60% to 95% by weight, and most preferably 70% to 85% by weight. Preferably the proportion of curable molecules in the mixture ranges from 2% to 60% by weight, more preferably 5% to 40% by weight, and most preferably 15% to 30% by weight. Preferably, the photoinitiator is present in the mixture in the proportions 0.5% to 5% by weight, more preferably 1% to 3% by weight. Preferably, the photoinitiator is also soluble in the dry mixture of adhesive and curable molecules, although it will be capable of exerting its curing initiating effect upon exposure to an activating light source if finely dispersed through the dry mixture but not dissolved in it.

The weight proportion for the adhesive is given here in terms of its dry weight and excludes any solvent which might normally be present in a commercially available bulk adhesive.

In certain embodiments, the weight proportion of adhesive is from one of the following lower endpoints (inclusive), or from one of the following upper endpoints (inclusive). The lower endpoints are 20%, 30%, 40%, 50%, 60% and 70%; the upper endpoints are 98%, 95%, 90% and 85%. In certain embodiments, the weight proportion of curable molecules is from one of the following lower endpoints (inclusive), or from one of the following upper endpoints (inclusive). The lower endpoints are 2%, 5%, 10% and 15%; the upper endpoints are 80%, 70%, 60%, 50%, 40% and 30%. In certain embodiments, the weight proportion of photoinitiator is from one of the following lower endpoints (inclusive), or from one of the following upper endpoints (inclusive). The lower endpoints are 0.05%, 0.1%, 0.2%, 0.5% and 1.0%; the upper endpoints are 10%, 5%, 4% and 3%.

The incidental constituents may be one or more of stabilisers, tackifiers, light scattering particles, fungicides, colorants, humectants, etc.

The adhesive component may be a hydrocolloid having polymeric chains extending from a core or nucleus, and the reference to the adhesive and the curable molecules being mutually soluble in each other when dry is to be understood as meaning that the curable molecules and the polymeric chains are mutually soluble in each other. Hydrocolloid-based medical dressings may be used for skin and wound treatment. When first attached to the skin, dry hydrocolloids are only slightly adherent to the skin, but quickly absorb moisture from the skin and become more tacky.

The preparation method for the switchable adhesive compositions of the invention is very simple. The adhesive component, the curable molecules (monomers and/or oligomers) and the photoinitiator are stirred together in darkness or under red light conditions for about 30 to 60 minutes, most conveniently at room temperature. The adhesive component is usually supplied in solution (typically, 40% to 60% solids by weight); the curable molecules are usually solvent free, although some curable molecules of high viscosity may be carried in a solvent; the photoinitiator is usually solid and the most difficult component of the system to dissolve and/or disperse.

Following completion of the stirring together, the resulting solution is spread onto a release liner at a certain thickness—typically about 60 μm when wet—and then left to dry at room temperature for about 10 minutes. The release liner may be a polyethylene coated paper with some silicone oil on it. The spread adhesive is then further dried at 80-150° C. for 3 to 10 minutes. A slightly higher temperature and a longer drying time can be used if necessary. After drying, the thickness of the spread adhesive will typically be about 30 μm.

The dried adhesive is then transferred onto a test substrate, such as a carrier film, for peel strength and switching evaluation.

Alternatively, the dried adhesive may be transferred to a material for a wound dressing, for example a web of polyethylene or polyurethane film which may optionally be perforated, or a woven or non-woven fabric.

For a medical dressing or similar application, the adhesive component may be selected from polymers capable of forming shaped bodies, thin walls or coatings. Suitable polymers are biologically and pharmaceutically compatible, hypoallergenic and insoluble in and compatible with body fluids or tissues with which the dressing is contacted.

Exemplary light transmitting materials for carrying the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated poly-ethylene, polyvinyl chloride, vinyl chloride-vinyl acetate copolymer, crosslinked polymethacrylate polymers (hydrogel), polyvinylidene chloride, poly (ethylene terephthalate), butyl rubber, epichlorohydrin rubbers, ethylenevinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoro-ethylene; and the like.

The adhesives may be water-soluble, but will most often be soluble in, and hence commercially supplied as solutions in, organic solvents such as ethyl acetate, hexane, toluene, acetone etc. Preferred adhesives are polyacrylates, polyurethanes and polysilicones. Especially preferred are polyacrylates. By the term polyacrylates is meant acrylate, methacrylate and acrylate copolymer adhesives. Indeed acrylate copolymer adhesives are most preferred, e.g. alkyl acrylate copolymers.

Any conventional known adhesive can be used as the adhesive component, including adhesives having unsaturated groups, e.g., natural rubber, polyisoprene and derivatives thereof. It is also possible to use, as the starting or base adhesive, one which is manufactured with bound-in curable groups; this is mixed with further curable molecules (not bound-in).

Preferably, the curable molecules and the adhesive are soluble in each other when in the dry state, i.e., in the absence of a solvent. Alternatively, in the case that the adhesive and the curable molecules are not mutually soluble in each other when dry, or are only partly mutually soluble, they are uniformly dispersed in the composition. Typically, the adhesive (or the base adhesive if a mixture of adhesives is used) will be selected from polyacrylates, polyurethanes and silicone adhesives.

In the broadest sense, any conventional known unsaturated compounds could be used as the curable molecules, but preferred examples, used alone or in mixtures, are curable molecules such as acrylic acid esters or methacrylic acid esters of alcohols, glycols, pentaerythritol, trimethylpropane, glycerol, aliphatic epoxides, aromatic epoxides including bisphenol A epoxides, aliphatic urethanes, silicones, polyesters and polyethers, as well as ethoxylated or propoxylated species thereof.

Most effective are curable molecules having more than one unsaturated site, i.e., greater than single functionality. Multiple functionalities of 4 or more are especially effective because curable molecules of this type are able to form highly cross-linked three-dimensional polymeric networks which are an important feature of switching, as will be explained below. Also, many curable molecules having multiple functionalities are commonly available at reasonable cost.

The photoinitiator may be any species which is capable of producing radical species under mild conditions, e.g. visible light, in order to promote radical polymerization reactions in the curable molecules. As a consequence, when the photoinitiator becomes activated by exposure to visible light, the curable molecules form chemical bonds with other curable molecules and hence create polymeric cross-linking. The effect of such cross-linking is to build a three-dimensional polymeric network entangling the adhesive polymer chains, thereby reducing their mobility and free volume. The photoinitiator may alternatively produce radical species under the mild conditions of long wave UV.

Curable molecules having multiple functionality are able to form highly cross-linked three-dimensional polymeric networks easily and hence exhibit good switching properties. The adhesive strength of the adhesive becomes reduced and it becomes less tacky so that it may be peeled more easily from the surface to which it is attached.

The adhesive mixture may also contain stabilisers which are added in order to prevent spontaneous crosslinking of the curable molecules during storage. Examples of such stabilisers are hydroquinones such as Methoxy phenol (sometimes referred to as hydroquinone monomethyl ether), or 1-Piperidinyloxy-4,4'-[1,10-dioxo-1,10-decanediyl)bis(oxy)]bis [2,2,6,6-tetra methyl] and Pentaerythritol tetrakis(3-(3,5-di-tert-butyl-4-hydroxyphenyl)propionate).

The adhesive mixture may also include photo-sensitisers. Since a sensitising species often absorbs energy in a different part of the spectrum from the initiator, more effective use of the light source may be achievable through the incorporation of sensitisers into the mixture. Many photo-sensitisers are complex organic molecules, absorbing in the visible portion of the spectrum.

The adhesive mixture may also incorporate light scattering particles to increase the effect of irradiation of the adhesive mixture. Preferably, the light scattering particles are an inorganic compound such as silica powder, alumina powder, silica-alumina powder or mica powder with particle sizes of the order of 10 nm or greater, typically up to 1 μm.

Any conventionally known free radical initiators may be used. Particularly preferred are those initiators which react to visible light radiation, although initiators which react under shorter wavelength light may be used in compositions of the invention, depending on the application. Thus, free radical initiators which may be mentioned include titanocene photoinitiators; dye/co-initiator systems, e.g., thionine/triethanolamine; dye/borate salt systems; dye/peroxide systems and 1,2-diketone/co-initiator systems, e.g., camphor-quinone/tertiary amine.

Examples of visible light photoinitiators (which include Irgacure 784 because it absorbs light both in the UV and visible spectrum) are: Benzildimethyl ketal; Phenanthrenequinone; Titanocenes (of which Irgacure 784 is one example); Bis(2,4,6-trimethyl-benzoyl)-phenylphosphineoxide.

Examples of UV photoinitiators are: Benzoin and ethyl, isopropyl or isobutyl ethers of Benzoin; Benzophenone and hydroxy or methyl benzophenones; 2-Methyl-1[4-(methylthio)phenyl]-2-morpholinopropan-1-one; Acetophenone and 4'-Phenoxyacetophenone; Benzoyl-biphenyl; Benzil; Anisoin, as well as the Irgacures such as Irgacure 651 (benzyl dimethyl ketal) or Irgacure 907 (2-methyl-1-[4-(methylthio) phenyl]-2-morpholino-propan-1-one); or the Uvatones, such as Uvatone 8302 (2,2-diethoxy-1,2-diphenyl ethanone).

Some photoinitiators contain phosphine compounds which will not receive approval by the medical regulatory authorities for use near the skin. However, phosphine-containing photoinitiators may be used in other, non-medical, applications.

Preferred free radical photoinitiators for medical applications are the titanocene initiators such as bis.(.eta.5-cyclopentadienyl)-bis(2,6-difluoro-3-[pyrrol-1-yl]-phenyl) titanium, sold in the UK by Ciba Geigy as Irgacure 784 (Trade Mark).

The present invention is not limited to use in adhesive dressings. Examples of other technical applications include:

| Application | Format | Description |
| --- | --- | --- |
| Labels, posters or Notices | A two or three-layer design as depicted in FIG. 3 or FIG. 1. | Labels comprising an adhesive according to the present invention can be used in product tags, pricing tags, advertisement posters put onto the varnish of vehicles. There will result a strong fixation and an easy removal without any adhesive residues left on the surface Or, in the case of a two layer film, easily removable residues after switching the remaining adhesive. |
| Protection Films | A two or three-layer design as depicted in FIG. 3 or FIG. 1. | Goods may get scratches during transportation, storage, handling etc; and by using an adhesive according to the present invention in combination with protective films, the goods will be protected from scratches and similar surface damage; when removing the film, no strong peeling force is necessary and, in the case of a three layer film, no adhesive residues left on the goods; or, in the case of a two layer film, easily removable residues after switching the remaining adhesive. |
| Fixation of Sensitive Parts During Manufacture or Transport | A three-layer design as depicted in FIG. 1. | Products and/or product parts that are very fragile and/or have a sensitive surface can be adhered to a substrate using an adhesive according to the present invention during transportation or manufacturing processes for achieving a very accurate position and fixation; after processing, the product can still be detached from the adhesive when desired without high peel forces and without leaving residues on its surface. |
| Shop Floor or Wall Marker Labels | A two-layer design as depicted in FIG. 3. | Using an adhesive according to the present invention on shop floor marker labels in different shapes, a very strong fixation to the floor or wall surface is possible. When the marker label is removed, adhesive residues may be left on the surface which are very easy to rub off when switched. |
| Wallpaper | A three-layer design as depicted in FIG. 1. | Using an adhesive according to the present invention on wall paper, a very strong fixation to the wall is possible. When the wallpaper is removed after switching the adhesive, the wall surface is left without any damage or residuals. |
| Masking or Fixation Tapes (fixation of non-fragile or non-delicate articles) | A two or three-layer design as depicted in FIG. 3 or FIG. 1. | Using an adhesive according to the present invention for the purpose of temporary fixation or masking, a very strong fixation to the surface is possible. When the tape is removed after switching the adhesive using a three layer design, the surface is left without any residues or, in the case of a two layer film, easily removable residues after switching the remaining adhesive. |
| De-bond on demand(DOD) applications, such as opening of packages and recycling of different materials in a product by detaching them after the end of service life time. | A two or three-layer design as depicted in FIG. 3 or FIG. 1. | Using an adhesive according to the present invention for the purpose of strongly attaching different components into a product or package. When the product or package needs to be disassembled, the light occlusive layer is removed and after switching the adhesive the different parts can easily be detached. Should adhesive residues be left on the component or product surface, these can be easily removed after switching the adhesive. |

Whilst it is preferable that the curable molecules in the mixture react via a free radical reaction, it is most desirable that the reaction of the curable molecules is visible light initiated through the use of suitable photoinitiators. Thus the wavelength of the light used may be less than 700 nm, e.g., preferably between 400 and 700 nm, particularly less than 550 nm.

The dosage of light used may vary depending upon the switchable adhesive composition. When a visible light switchable adhesive is used, ambient light may be used and therefore the dosage may vary according to the prevailing lighting conditions. When UV light is used, the dosage is generally greater than 0.4 mW.cm-1.

In a second aspect, the present invention provides a device or article incorporating the switchable adhesive formulation of the first aspect of the invention. In particular, the device may be a medical device such as a first aid product, an ostomy device, intravenous (IV) tape, other surgical tapes and adhesive bandages, patches which deliver therapeutic agents transdermally, skin closure products, wound dressings, etc.

For medical applications, the curable molecules used in the switchable adhesive preferably have a molecular mass greater than 500 dalton (Da), more preferably greater than 1000 Da, most preferably greater than 1500 Da. Molecules of this size are generally understood to be incapable of being absorbed through the skin and hence are less hazardous.

The adhesive mixtures of the invention are preferably pressure sensitive adhesives (PSAs) and are particularly advantageous in the manufacture of adhesive medical devices as mentioned above. The adhesives may also be useful in the manufacture of other conventional products which require a peelable adhesive, e.g., masking tapes, stencils, etc.

According to a further feature of the invention an adhesive dressing is provided comprising a backing layer substantially coated on at least one surface thereof with an adhesive as hereinbefore described. The adhesive coating may be a continuous coating or a non-continuous coating, e.g., the adhesive may be spread in a pattern. A non-continuous coating is helpful, for example, in improving air circulation and may assist in rendering wound dressings and surgical tapes "breathable".

The backing layer preferably comprises a light occlusive layer and a transparent or translucent layer. By the term light occlusive layer is meant, in particular, a layer which is occlusive over the wavelength range in which the photoinitiator absorbs. Especially preferred is a light occlusive layer that is visible light occlusive. The light occlusive and transparent layers, if comprised of similar materials, may be laminated together by lightly pressing them together at the nip of a pair of heated rollers. Alternatively, they may be bonded together using a low peel strength adhesive on the surfaces facing each other. Preferably, the light occlusive layer has the low peel strength adhesive on its surface facing the transparent layer and the low peel strength adhesive remains attached to the light occlusive layer when the layers are peeled apart.

The breathability properties of the backing layer must be such that it doesn't block water transmission, otherwise the skin will get very moist underneath the dressing. This may be detrimental to the health of the underlying tissues and/or may result in loss of adhesion of the dressing prematurely.

Thus, in accordance with the second aspect of the invention mentioned above, an adhesive dressing using the inventive adhesive may be applied to the skin of a patient. When it is desired to remove or replace the dressing, the light occlusive layer part of the backing layer may be removed. The adhesive on the skin-facing surface of the transparent layer can then be exposed to either ambient light or an artificial light source, such as an incandescent lamp, a fluorescent lamp, LEDs, etc. After a given time the peel strength of the adhesive will be reduced, allowing the transparent layer to be removed from the patient's skin.

Thus, a dressing is provided as hereinbefore described comprising a backing layer and an adhesive layer, wherein the backing layer comprises a removable light occlusive layer and a transparent layer intermediate the occlusive layer and the adhesive layer and wherein the adhesive layer comprises a switchable adhesive as hereinbefore described.

Any conventional known occlusive and transparent materials may be used in the backing layer of the dressings of the invention. Preferred dressings are those which comprise a film backing layer, i.e., both the occlusive and transparent layers comprise a film, although other backing layers such as fabric layers may be used.

The term "film" in this context means a thin sheet or web of material. Typically, it could be a thermoplastic polymer. In some circumstances, a metal foil could be used for the occlusive layer, for example where the transportation or diffusion of moisture is of no importance.

Dressings of the invention may be manufactured using conventional methods, save for the use of the inventive adhesive in place of a conventional adhesive and the requirement not to expose the adhesive mixture to light. The occlusive layer of the backing layer may be adhesively bonded to the transparent layer or may be laminated thereto. The peel force required to remove the occlusive layer from the transparent layer must be less than that of the switchable adhesive in its tacky form.

Dressings of the invention are especially useful in the treatment of wounds. Thus, according to a further feature of the invention, the invention provides a method of treating a wound on a patient comprising applying a dressing as hereinbefore described to the wound of a patient. The method may also include the removal of the dressing by removing the light occlusive layer of the dressing and then irradiating the adhesive through the transparent or translucent layer to render the adhesive non-tacky.

Various medicinal agents may be incorporated into the adhesive compositions of the present invention. By medicinal agent is meant pharmacologically active agents including agents which are topical anaesthetics such as xylocaine, bacteriostatic agents such as silver nitrate; anti-bacterial agents of which preferred forms are silver sulphadiazine and chlorhexidine salts; antibiotics; topical steroids, enzymes; tissue stimulants; coagulants and anticoagulants and antifungal agents. Other agents such as emollients may also be added. The effect of such agents may contribute to the method of treatment using dressings of the invention.

The invention will now be illustrated by way of example only with reference to the drawings, in which.

Figure 1:
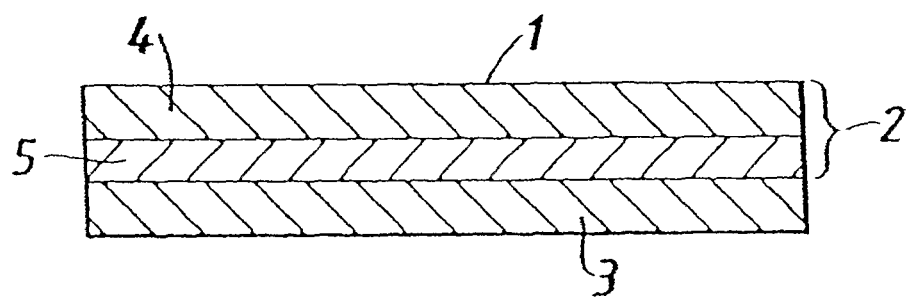
FIG. 1 is a cross-section of an adhesive tape using a switchable adhesive in accordance with the invention.

Referring to FIG. 1, an adhesive tape is designated by reference numeral 1. The tape comprises a backing layer 2 and an adhesive layer 3. The backing layer 2 comprises an occlusive layer 4 and a transparent layer 5 intermediate the occlusive layer 4 and the adhesive layer 3. The tape may optionally be provided with appropriate carrier layers and protector layers.

Such an adhesive tape could be in the form of a surgical tape for medical applications. In use, the tape 1 is adhered to the skin of a patient when the adhesive layer 3 is in a tacky state. When it is desired to remove the tape 1 from the patient's skin, the occlusive layer 4 is removed to reveal the transparent layer 5 and thereby expose the adhesive layer 3 to visible light. The visible light causes the photoinitiator to initiate free-radical cross-linking of the pressure sensitive adhesive through the curable molecules incorporated in the adhesive mix. This results in the adhesive losing its tackiness and peel strength. The time required for complete switching of the adhesive from the tacky state to the non-tacky state may vary, e.g., from a few seconds to several minutes. The tape may then be removed from the patient's skin with reduced trauma to the patient.

Figure 2:
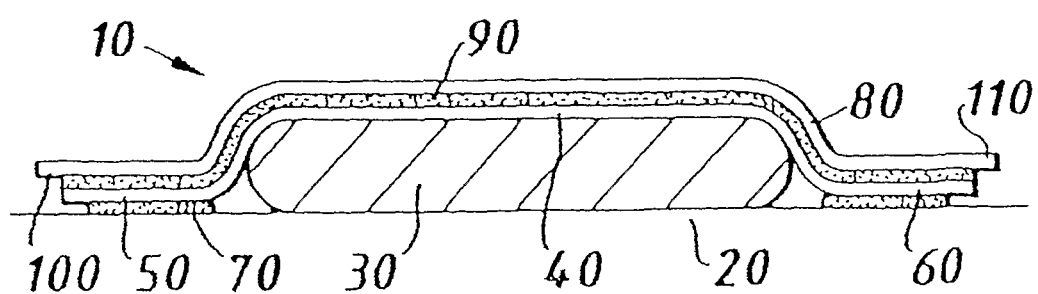
FIG. 2 is a cross-section of a dressing of the invention.

Referring now to FIG. 2, this shows a schematic cross-section of a medical dressing according to the present invention when in use on a patient.

Medical dressing 10 is shown attached to a patient's skin 20. The dressing 10 comprises a wound facing absorbent layer 30 disposed beneath a protective backing layer 40. At opposed edges 50, 60, the backing layer 40 is provided with adhesive 70 which comprises groups that can be cross-linked under the influence of visible and/or UV light.

The backing layer 40 is provided with a cover 80 which is releasably secured to the backing layer 40 by a weak adhesive 90. In an alternative arrangement, not shown here, the cover 80 may be laminated to the backing layer 40. For ease of removal, the cover 80 overlaps the backing layer 40 at its edges 100, 110.

When it is desired to remove the dressing from the skin of the patient, the cover 80 can be gripped at its edges 100, 110 and peeled from the backing layer 40 to expose the adhesive 70 to UV or visible light irradiation. This irradiation acts so as to generate free radicals that cause the curable molecules to undergo a curing reaction which, after a certain time (depending upon the adhesive used), causes the adhesive 70 to lose its tackiness to such an extent that the dressing can be removed without causing trauma to the patient.

In order that the removal of the cover 80 does not itself cause trauma to the patient, the peel strength of the adhesive 90 adhering the cover 80 to the backing layer 40 should be less than the peel strength of the adhesive 70 adhering the dressing 10 to the patient's skin.

Since the adhesive 70 loses tackiness on exposure to visible and/or UV light, it is desirable that the adhesive 70 is not exposed to the light for a substantial period when the dressing 10 is applied to a patient. Thus, the adhesive 70 may be initially provided on the surface with release paper (not shown) which is preferably opaque to UV and visible light and which can be readily removed from the adhesive so that the dressing is ready for use when required.

It is another requirement of the constituents of the adhesive mixture used in medical applications that they should be capable of undergoing sterilisation without causing switching of the adhesive from its tacky state to a non-tacky state.

Figure 3:
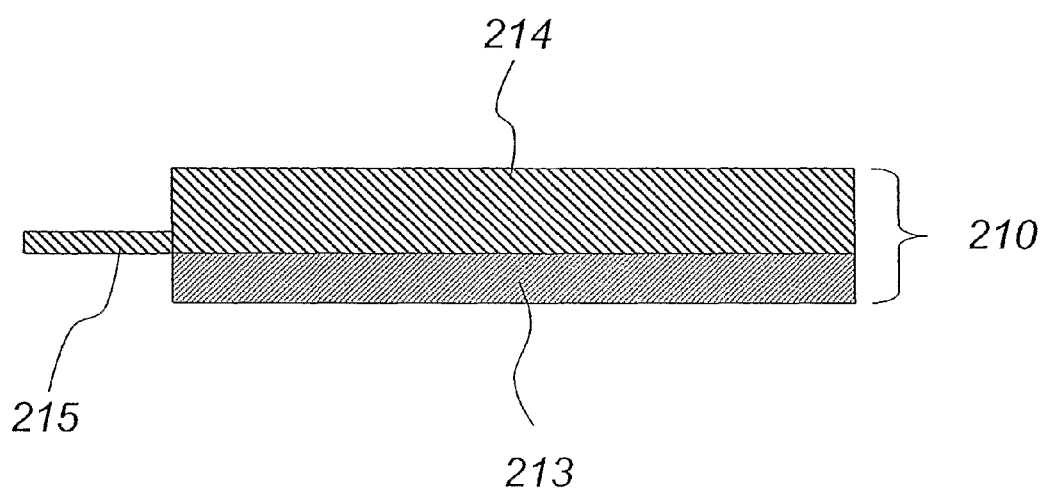
FIG. 3 is a schematic cross-sectional view of a simple adhesive label using the switchable adhesive of the invention.

Turning now to FIG. 3, this shows in a schematic cross-sectional view how the invention can be applied to a simple two-layer device such as a removable product label.

The label is generally denoted by the reference 210 and comprises an adhesive layer 213 composed of switchable adhesive in accordance with the present invention, and an occlusive layer 214 (which may be in the form of a film) overlying the adhesive layer and preventing access of light to the adhesive layer. In this embodiment, the occlusive layer is also provided with a peel tab 215 that facilitates removal of the label from the product surface to which it is applied.

It is not essential in the case of a removable product label for the peel force required to remove the occlusive layer to be less than the peel force required to remove the adhesive in its tacky form from the product. In practice, it may be preferred if some of the adhesive layer is removed with the occlusive layer. The residue of the adhesive which remains on the product is then able to switch to its non-tacky state through exposure to light. The non-tacky adhesive residue can be easily removed from the product surface by rubbing or washing.

The occlusive layer 214 may have a design/indicia on its surface. In some embodiments, the design/indicia may provide the occlusive effect and may therefore be disposed at the interface between the occlusive layer 214 and the adhesive layer 213 so that it is protected from scuffing damage.

As mentioned above, one problem associated with switchable adhesives having bound-in curable groups is that they require painstaking synthesis. Also, they often require switching times of more than 1 minute. In particular, the polymerisation of acrylate internally functionalised switchable adhesives requires the use of multiple solvents, firstly in order to produce a polymer having a sufficiently high molecular weight and low monomer concentration for suitability as a medical adhesive, and secondly to carry out the reaction of the functionalising moiety with the main polymer chain.

An adhesive manufacturing process requiring multiple solvents, and hence solvent exchange steps, is complicated, time consuming and expensive.

By contrast, the switchable adhesives of the present invention can be made from a mixture of readily available adhesives and curable monomers or oligomers containing acrylate functions which, upon irradiation, form chemical bonds between the oligomers or monomers and hence create polymeric cross linking. The effect of such cross linking is to build a three-dimensional polymeric network interlocking with the adhesive polymer chains, thereby reducing their mobility and free volume. This change, which takes place very quickly, causes the PSA to become low tack. The force required to peel the adhesive has been found to reduce considerably, by at least 60% to 90%, after illumination.

Examples of suitable curable monomers and oligomers, used alone or in mixtures, are acrylic acid esters or methacrylic acid esters of alcohols, glycols, pentaerythritol, trimethylpropane, glycerol, bisphenol A epoxides, aliphatic epoxides, aromatic epoxides, aliphatic urethanes, aromatic urethanes, silicones, polyesters and polyethers as well as ethoxylated or propoxylated species thereof.

The invention will now be further illustrated with reference to Examples. In the Examples below, the constituents are listed in the order:
1 base adhesive
2 curable molecules
3 photoinitiator and, where present,
4 stabiliser.

EXAMPLE 1

| | Component | Amount (g) |
|---|---|---|
| 1 | GMS 788 | 50 |
| 2 | CN 925 | 5 |
| 3 | Irgacure 784 | 0.5 |

EXAMPLE 2

| | Component | Amount (g) |
|---|---|---|
| 1 | GMS 788 | 30 |
| 2 | CN 925 | 4 |
| 3 | Irgacure 784 | 0.1 |
| 4 | Irganox | 0.02 |

EXAMPLE 3

| | Component | Amount (g) |
|---|---|---|
| 1 | Aroset 1450 Z 40 | 30 |
| 2 | CN 925 | 12 |
| 3 | Irgacure 784 | 0.5 |
| 4 | Irganox | 0.08 |

EXAMPLE 4

| | Component | Amount (g) |
|---|---|---|
| 1 | GMS 788 | 30 |
| 2 | Ebecryl 870 | 3 |
| 3 | Irgacure 784 | 0.3 |
| 4 | Irganox | 0.02 |

EXAMPLE 5

| | Component | Amount (g) |
|---|---|---|
| 1 | Duro-Tack 180-129A | 20 |
| 2 | CN 925 | 2.5 |

-continued

| | Component | Amount (g) |
|---|---|---|
| 3 | Irgacure 784 | 0.25 |
| 4 | Irganox | 0.02 |

EXAMPLE 6

| | Component | Amount (g) |
|---|---|---|
| 1 | Polytex SP 8002 | 40 |
| 2 | CN925 | 5 |
| 3 | Irgacure 784 | 0.5 |
| 4 | Irganox | 0.03 |

EXAMPLE 7

| | Component | Amount (g) |
|---|---|---|
| 1 | GMS 1753u | 40 |
| 2 | EtoxPETA | 16 |
| 3 | Irgacure 819 | 0.5 |
| 4 | MEHQ | 0.03 |

TABLE 1

Table of Suppliers

| Component | Description | Company |
|---|---|---|
| GMS 788 | Pure acrylic adhesive, dry content 42% | Cytec Surface Specialties |
| GMS 1753u | Pure acrylic adhesive, dry content 42% | Cytec Surface Specialties |
| CN 925 | Aliphatic urethane tetraacrylate | Sartomer Co., Inc. (Cray Valley SA) |
| EtoxPETA | Tetraethoxylated Pentaerythritol Tetraacrylate | Sartomer Co., Inc. (Cray Valley SA) |
| Irgacure 784 | Bis(.eta.5-cyclo-pentadienyl)-bis (2,6-difluoro-3-[pyrrol-1-yl]-phenyl) titanium | Ciba Specialty Chemicals |
| Irgacure 819 | Bis(2,4,6-trimethylbenzoyl)- phenylphosphineoxide | Ciba Specialty Chemicals |
| Irganox 1010 | Pentaerythritol Tetrakis(3-(3,5-di- tert-butyl-4-hydroxyphenyl) propionate | Ciba Specialty Chemicals |
| Aroset 1450 Z 40 | Thermosetting acrylic solution polymer, dry content 40% | Ashland Inc. |
| Polytex SP 8002 | Acrylic-base adhesive, dry content of 45% | Avery Dennison Materials Europa |
| Ebecryl 870 | Hexafunctional polyester acrylate | Cytec Surface Specialties |
| Duro-Tack 180- 129A | Self curing polyacrylate adhesive, dry content 50% | Henkel Adhesive Technologies |
| Hostaphane RNK 2600 | Polyester film | Mitsubishi Polyester Film |

Preparative Details

All components in the respective examples were loaded into a sealable glass jar and mixed to a homogenous solution over a period of approximately 60 minutes under red light conditions using a magnetic stirrer. The resulting adhesive solution was then spread onto a release liner using a spreader to a coating thickness of about 60 μm and left to dry at room temperature for 10 minutes.

The adhesive coating was then further dried in a ventilated fan assisted oven at 110° C. for an additional 10 minutes, except for Example 3 which was dried for 30 minutes at 100° C. After drying, the thickness of the adhesive coating was about 30 μm.

Finally, a 23 μm Hostaphane RNK 2600 (polyester) film was transferred to the exposed side of the adhesive in preparation for peeling studies. All procedures using Irgacure 784 were carried out under red light conditions.

Peel Force Measurements

Peel strengths were determined after a dwell time of 20 minutes using a LLOYD testing rig (L2000R) according to FINAT test method FTM1, with the exception that high density polyethylene (HDPE) plates were used as the substrate and that a peeling rate of 100 mm/min was used in order to collect all of the necessary data within the time frame of one peel force measurement.

Adhesive switching was achieved by exposing the adhesive film (adhered to the HDPE plate) to light through the PET carrier film backing with a light intensity of approximately 12000 lux from a 500 W halogen lamp having a broad spectrum. It should be noted that switching times achievable with a light source intended for consumers (LEDs with spectra adjusted to the photoinitiator) will be less than the values obtained with the broad spectrum lamp mentioned above. However, using a light source in these tests that is adjusted to the photoinitiator would make it difficult to get an accurate measurement of the switching time for purposes of comparison, since the switching times would all have been very short. Switching times for the different coatings were measured as the time between the starting time of irradiation and the time when the substantially instantaneous loss of tack occurred, during a continuous peel strength test of about 1 minute (i.e., the adhesive was peeled for a period of time whilst being irradiated). Peel strengths and switching times were measured in quadruple and the average values of switch time and peel strength (before and after switch) were calculated.

Adhesive Switching

Results quoted below in Table 2 as %-switch refer to the percentage reduction in peel strength after exposure to light, calculated as follows:

$$(1 - P1/P2)*100 = \%\text{-switch}$$

where P1 is the peel strength after exposure to light and P2 is the initial peel strength.

TABLE 2

Results of Peel Strength Tests

| Example Number | Peel force before switch (N/25 mm) | Peel force after switch (N/25 mm) | Switch time (Seconds) | %-switch |
|---|---|---|---|---|
| 1 | 22.5 | 3.8 | 9.9 | 83 |
| 2 | 13.7 | 4.9 | 40.5 | 64 |
| 3 | 2.3 | 0.2 | 3.6 | 91 |
| 4 | 32.8 | 3.7 | 6.5 | 88 |
| 5 | 17.6 | 1.6 | 3.8 | 91 |
| 6 | 13.9 | 1.7 | 11 | 88 |
| 7 | 12 | 0.1 | 2 | 99 |

The adhesive of Example 7 is particularly suitable for labels because it has a high tack, very easily removable residuals and a very high switch percentage. It is probably not suitable for skin applications.

Figure 4:
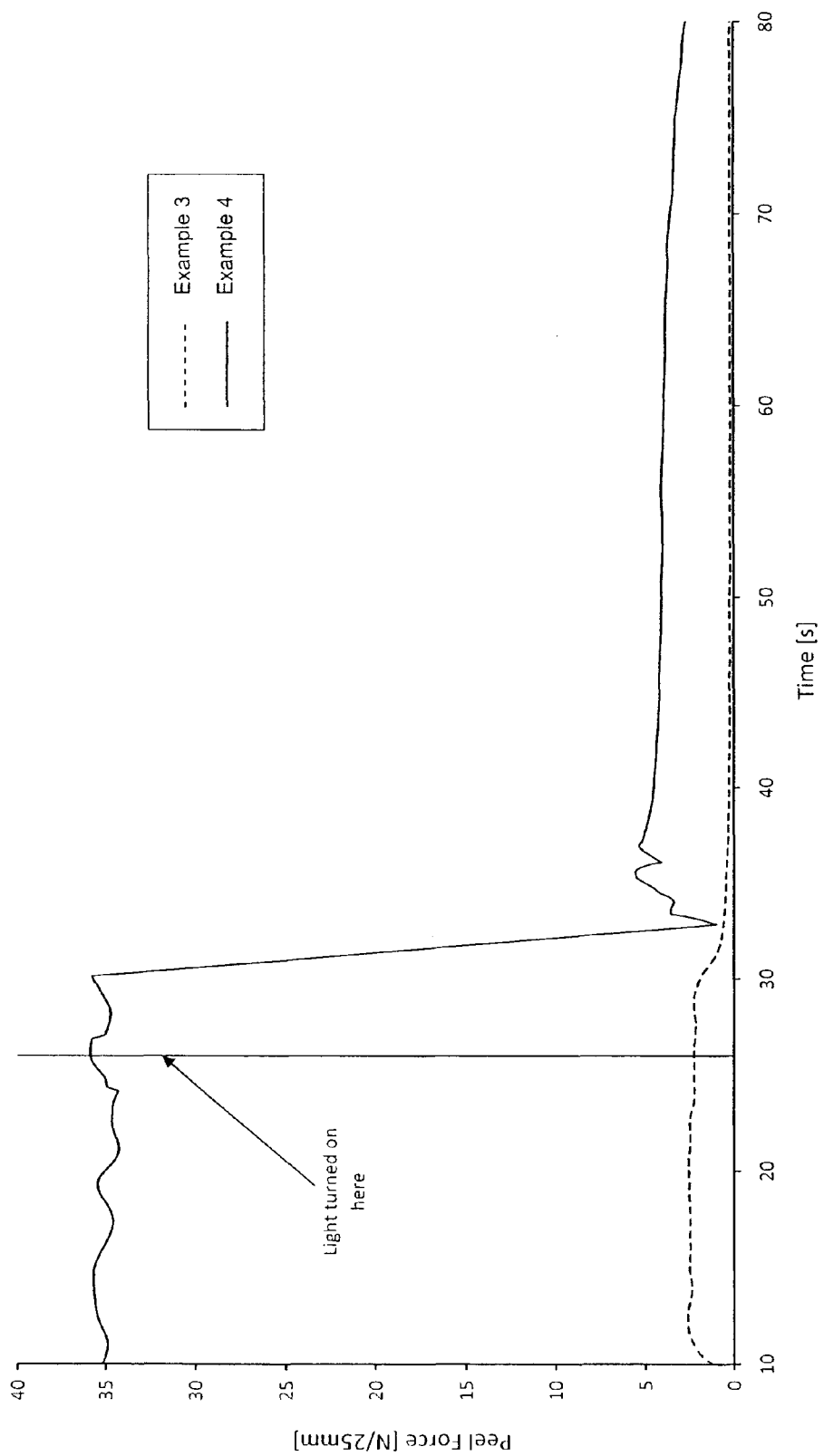
FIG. 4 is a graph of peel force against time for two examples of switchable adhesive according to the invention, showing the reduced peel force after switching.

FIG. 4 is a graph of peel force against time for Examples 3 and 4, showing how the peel force reduces significantly within a few seconds of exposing the adhesive to light.

Example 4 is an example of an adhesive composition which might find application in a medical dressing for use in treating a chronic wound or a permanent stoma that needs dressing repeatedly and where, if a non-switchable adhesive were used, skin trauma would be significant. The adhesive of Example 4 exhibits strong adhesion in the un-switched state but, after switching, the peel force is significantly reduced and a medical dressing using this adhesive could be easily removed after switching without causing discomfort to the patient or traumatising fragile skin.

Example 3 is an example of an adhesive suitable for very sensitive materials e.g. delicate production line work. The adhesive has an initial tackiness which is sufficient to position components reliably on a production line for certain steps in a production process. An occlusive layer may be removed at this low tackiness without perturbing the components. After switching, the peel force reduces to an almost negligible value, allowing the processed components to be removed easily from the production line.

The present invention is not limited to use in adhesive dressings. Examples of other technical applications include: removable labels; for shipping and handling of fragile or sensitive parts; production line applications where one or several pieces attached to a switchable PSA tape can be mounted into a structure—the tape can then easily be removed after irradiation. Other examples are vehicle labels, shop floor markers, wallpaper and adhesive fixings for posters and/or notices.

The invention claimed is:

1. A switchable adhesive composition comprising a mixture, in proportions by weight based on the weight of the composition, of:
   20% to 98% of adhesive;
   2% to 80% of curable molecules, and
   0.05% to 10% of photoinitiator,
   wherein the weight proportion of the adhesive is calculated on the basis of its dry weight,
   and wherein the curable molecules are not bound-in to the adhesive.

2. A switchable adhesive composition as claimed in claim 1 comprising a mixture, in proportions by weight based on the weight of the composition, of:
   40% to 98% of adhesive;
   2% to 60% of curable molecules, and
   0.5% to 5% of photoinitiator.

3. A switchable adhesive composition as claimed in claim 1 comprising a mixture, in proportions by weight based on the weight of the composition, of:
   60% to 95% of adhesive;
   5% to 40% of curable molecules, and
   0.5% to 5% of photoinitiator.

4. A switchable adhesive composition as claimed in claim 1 comprising a mixture, in proportions by weight based on the weight of the composition, of:
   70% to 85% of adhesive;
   15% to 30% of curable molecules, and
   1% to 3% of photoinitiator.

5. A switchable adhesive composition as claimed in claim 1 wherein the adhesive component is a mixture of adhesives having a base adhesive selected from the group consisting of polyacrylates, poly-urethanes and polysilicones.

6. A switchable adhesive composition as claimed in claim 5 wherein the base adhesive is a polyacrylate.

7. A switchable adhesive composition as claimed in claim 1 wherein the curable molecules are unsaturated compounds.

8. A switchable adhesive composition as claimed in claim 7 wherein the curable molecules are selected from the group consisting of acrylic acid esters or methacrylic acid esters of alcohols, glycols, pentaerythritol, trimethylpropane, glycerol, aliphatic epoxides, aromatic epoxides including bisphenol A epoxides, aliphatic urethanes, silicones, polyesters and polyethers, including ethoxylated or propoxylated species thereof, and mixtures thereof.

9. A switchable adhesive composition as claimed in claim 1 wherein the photoinitiator is selected from the group consisting of titanocene photoinitiators; dye/co-initiator systems including thionine/triethanolamine; dye/borate salt systems; dye/peroxide systems and 1,2-diketone/co-initiator systems, including camphor-quinone/tertiary amine.

10. A switchable adhesive composition as claimed in claim 1 wherein the photoinitiator is reactive to visible light.

11. A switchable adhesive composition as claimed in claim 1 wherein the reduction in peel force of the adhesive composition after switching is 30 to 98%.

12. A method for manufacturing a switchable adhesive composition comprising:
   stirring an adhesive component, curable molecules and a photoinitiator together in darkness or under red light conditions for 30 to 60 minutes at a temperature from 10° C. to 40° C. to form a switchable adhesive composition comprising a mixture in proportions by weight based on the weight of the composition, of: 20% to 98% of adhesive; 2% to 80% of curable molecules, and 0.05% to 10% of photoinitiator, wherein the weight proportion of the adhesive is calculated on the basis of its dry weight, the curable molecules are not bound-in to the adhesive component.

13. A method for manufacturing a switchable adhesive composition as claimed in claim 12 wherein the stirring temperature is room temperature.

14. A method for manufacturing a switchable adhesive composition as claimed in claim 12 further comprising drying the composition at 80° C. to 150° C.

15. A method for manufacturing a switchable adhesive as composition claimed in claim 14 further comprising spreading the composition onto a release means and drying it.

16. An adhesive product comprising:
   a backing layer coated on at least one surface thereof with a switchable adhesive composition comprising a mixture, in proportions by weight based on the weight of the composition, of: 20% to 98% of adhesive component; 2% to 80% of curable molecules, and 0.05% to 10% of photoinitiator, wherein the weight proportion of the adhesive is calculated on the basis of its dry weight and wherein the curable molecules are not bound-in to the adhesive component.

17. A product according to claim 16 wherein the backing layer comprises a light occlusive layer and a transparent or translucent layer.

18. A product according to claim 17 wherein the backing layer comprises a removable light occlusive layer and a transparent or translucent layer intermediate the adhesive layer and the light occlusive layer.

19. A product as claimed in claim 16 which is an adhesive medical dressing.

20. A method of treating a wound on a patient comprising:
   applying an adhesive medical dressing to the wound of the patient, wherein the adhesive medical dressing comprises a backing layer coated on at least one surface thereof with a switchable adhesive composition comprising a mixture, in proportions by weight based on the weight of the composition, of: 20% to 98% of adhesive component; 2% to 80% of curable molecules, and 0.05% to 10% of photoinitiator, wherein the weight proportion of the adhesive is calculated on the basis of its dry weight and wherein the curable molecules are not bound-in to the adhesive component.

* * * * *